United States Patent
Yagi

(10) Patent No.: US 6,542,349 B2
(45) Date of Patent: Apr. 1, 2003

(54) PORTABLE X-RAY FLUORESCENCE ANALYZER

(75) Inventor: Shigeki Yagi, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/827,121

(22) Filed: Apr. 5, 2001

(65) Prior Publication Data

US 2001/0038520 A1 Nov. 8, 2001

(30) Foreign Application Priority Data

Apr. 6, 2000 (JP) .......................... 2000-104845
Feb. 19, 2001 (JP) .......................... 2001-041316

(51) Int. Cl.$^7$ .............................................. H02P 3/10
(52) U.S. Cl. ............................................... 361/246
(58) Field of Search ................................. 361/245, 246

(56) References Cited

U.S. PATENT DOCUMENTS 4,186,337 A * 1/1980 Volk et al.

* cited by examiner

Primary Examiner—Edward H. Tso
(74) Attorney, Agent, or Firm—Adams & Wilks

(57) ABSTRACT

To provide a DC source drive type portable X-ray fluorescence analyzer having a simple source supply operation. A power supply input section of a DC power supply driven portable X-ray fluorescence analyzer, comprising polarity discrimination means 3 for discriminating the polarity of a DC power supply input to a DC power supply input terminal 1 and a DC power supply input terminal 2, and polarity display means 4 for displaying the polarity of the input DC power according to the output of the polarity discriminating means 3. There is also provided reverse connection protection means 5 for preventing supply of current to a load side when input indicating that the DC power supply has reverse polarity is detected from the polarity discrimination means 3. There is further provided switch means 6 for switching a current path of input current and supplying a correct polarity power supply to a load when input indicating that the DC power supply has reverse polarity is detected from the polarity discrimination means 3.

11 Claims, 4 Drawing Sheets

PORTABLE X-RAY FLUORESCENCE ANALYZER

BACKGROUND OF THE INVENTION

The present invention relates to a portable X-ray fluorescence analyzer driven by a DC source such as a battery.

Portable X-ray fluorescence analyzers are often used in cases of outdoor elementary analysis, such as archaeological sample examination, criminal field searches, fire patrol searches, scrap article inspection, etc. In order to be able to use an X-ray analyzer anywhere, it must be made capable of being driven by a DC power source such as a battery. A DC power source basically carries out supply from a dedicated DC power supply unit through an attached power supply cable, but as long as it is possible to supply power within specifications appropriate for the analyzer at a correct polarity, it is also possible to use a normal battery or a cigarette lighter terminal in an automobile, making it possible to select the power supply method according to circumstances.

In the case of supplying power for a portable X-ray fluorescence analyzer of the related art from outside a dedicated power supply unit, it is necessary to supply power with specifications appropriate to the analyzer, as described above, at the correct polarity. Otherwise, not only will the analyzer not operate, it may also be damaged.

Accordingly, when supplying DC power to the analyzer, it is essential to verify the polarity of a terminal voltage of an analyzer side connector of a power supply cable using a tester or the like, and if the result of this verification procedure is opposite to the input voltage polarity designated by the analyzer it is necessary to make it possible to install the correct power supply connection by changing connection of the power supply cable at the power supply side, or changing the wiring of the power supply cables. Supply of power to the analyzer is a critical operation, which means that at the time of setting up the portable X-ray fluorescence analyzer this operation is carried out carefully even if it is required to be completed in a short time. However, the time taken by the operation for the power supply is a problem with respect to a portable X-ray fluorescence analyzer where mobility is an important consideration.

Particularly with criminal field searches and fire patrol searches etc., there are cases where a sample whose characteristics are constantly changing is analyzed, and setting up the analyzer quickly and when to start measurement are important points.

The present invention has as its object to provide an extremely safe portable X-ray fluorescence analyzer, to solve the above described problems.

SUMMARY OF THE INVENTION

In order to achieve the above described object, the present invention is a DC power supply driven portable X-ray fluorescence analyzer provided with a power supply input section, comprising polarity discrimination means for discriminating the polarity of a DC power supply input to the power supply input section, and polarity display means for displaying the polarity of the input DC power according to the output of the polarity discriminating means.

There is also provided reverse connection protection means for preventing supply of current to a load side when an input indicating that the DC power supply has negative polarity is detected from the polarity discrimination means.

There is further provided switch means for switching a current path of input current and supplying a correct polarity power supply to a load when an input indicating that the DC power supply has negative polarity is detected from the polarity discrimination means.

The polarity of a DC power source input to a power supply input section of a DC power source driven portable X-ray fluorescence analyzer is displayed. Supply of input current to a load side is prevented when the DC power source is input with the reverse polarity. Also, if an input current path is changed by a polarity change switch, power of the correct polarity is supplied to the load.

DETAILED DESCRIPTION OF THE PREFERRED EMBODIMENT

First Embodiment

An embodiment of the present invention will be described in the following based on the drawings.

Figure 1:
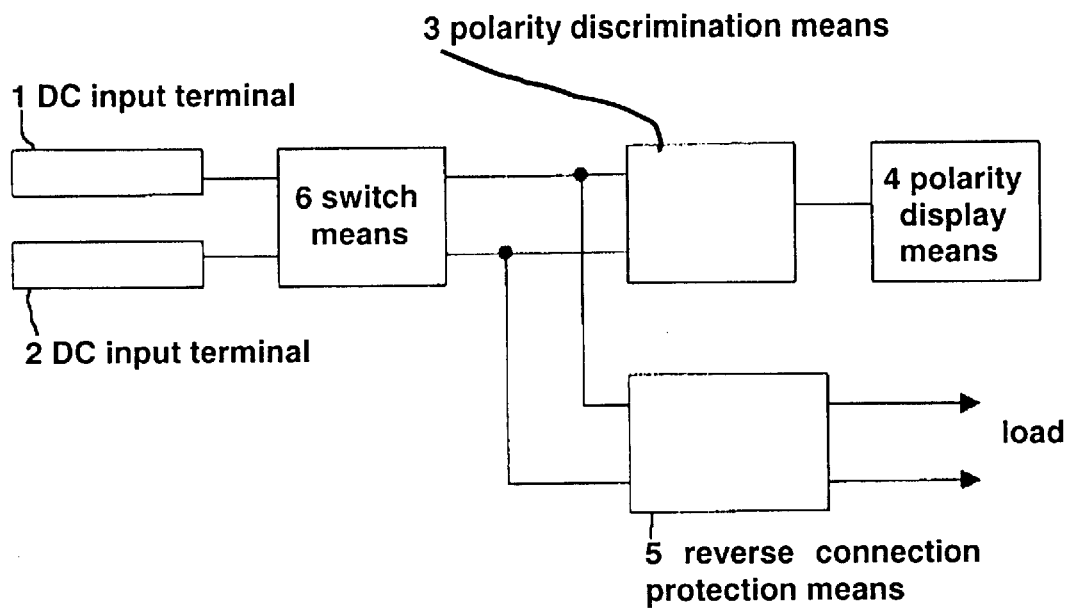
FIG. 1 is a block diagram of a power supply input section of a DC source drive type portable X-ray fluorescence analyzer.

FIG. 1 is a block diagram of a power supply input section of a DC source drive type portable X-ray fluorescence analyzer. The polarity of a DC source input to a DC source input terminal 1 and a DC source input terminal 2 is discriminated by polarity discrimination means 3. The result of this discrimination is output to polarity display means 4 and reverse connection protection means 5. The polarity display means displays the polarity of the input DC power supply according to output from the polarity discrimination means 3. The reverse connection protection means 5 supplies DC power directly to the load when DC power of the correct power is input, but if DC power of the reverse polarity is input, supply of DC power to the load is interrupted. When DC power of a reverse polarity is input, the switch means 6 changes an input current flow path, and reverses the polarity of the input DC power source to supply DC power of the correct polarity to the load.

Figure 2:
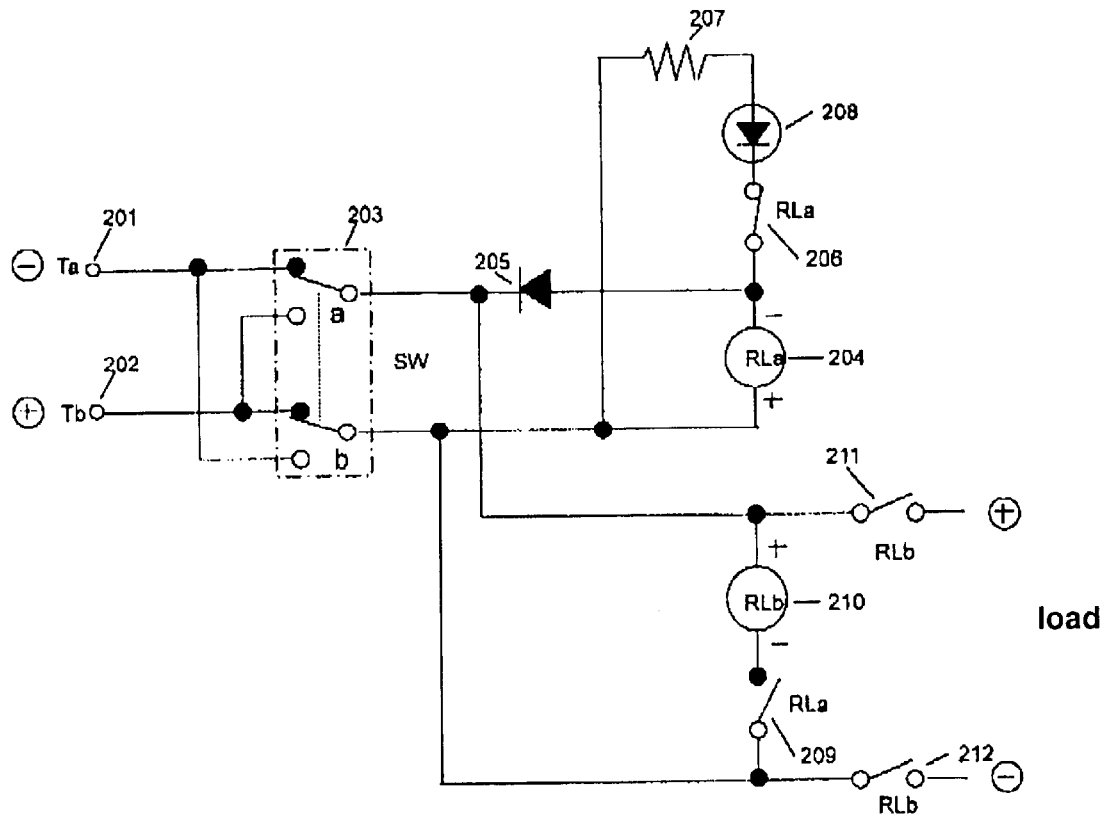
FIG. 2 is a circuit diagram of a power supply input section of a DC source drive type portable X-ray fluorescence analyzer of the present invention.

FIG. 2 is a circuit diagram specifically showing the power supply input section of this embodiment. In this drawing, the state where the DC power source is reversely connected is shown. With a power supply input terminal Ta 201 as a reference, a correct DC voltage is supplied to power supply input terminal Tb202. As a result, current flows through a path from Tb202 > a contact point on side b of switch 203 > a relay a 204 > a diode 205 > a contact point on side a of switch 203 > Ta201, and the contact point 206 of relay a is closed. As a result, current flows through a path from Tb202 > a contact point on side b of switch 203 > a resistor 207 > an LED 208 > the contact point 206 of relay a > the diode 205 > a contact point on side a of switch 203 > Ta201, and the LED 208 is illuminated. The flow of current through the path from Tb202 > the contact point on side b of switch 203 > the relay a 204 > the diode 205 > the contact point on side a of switch 203 > Ta201, is due to the diode 205 being inserted in a forward direction along the current path. As a result, in a reverse path, namely a path through TA201, the contact point on the a side of switch 203, the diode 205, the relay a204 the contact point on the b side of the switch 203 and Tb202, the diode 205 is connected in the reverse direction and so current does not flow. That is, the circuit linking Ta201, the contact point on the a side of switch 203, the diode 205, the relay a 204, the contact point on the b side of the switch 203 and Tb202 constitutes the polarity discrimination means, and as a result of polarity discrimination the contact point 206 of the relay a is closed or opened. In FIG. 2, the DC power source is reversely connected, and as a result the contact point 206 of the relay a is closed, and the LED 208 is illuminated. That is the LED 208 constitutes the polarity display means, and when the LED is illuminated it indicates that the DC power supply is reversely connected. On the other hand, another contact point 209 of the relay a is open, and so current does not flow in the relay b210. Since the contact points 211 and 212 of the relay b remain open at this time, a supply path of the input DC power source to the load is disconnected. Accordingly, the circuit linking the TA 201, the contact point on the a side of the switch 203, the relay 210, the contact point 209 of the relay b, the b side contact of the switch 203 and Tb202, and the contact points 211 and 212 of the relay b, constitute the reverse connection protection means.

Figure 3:
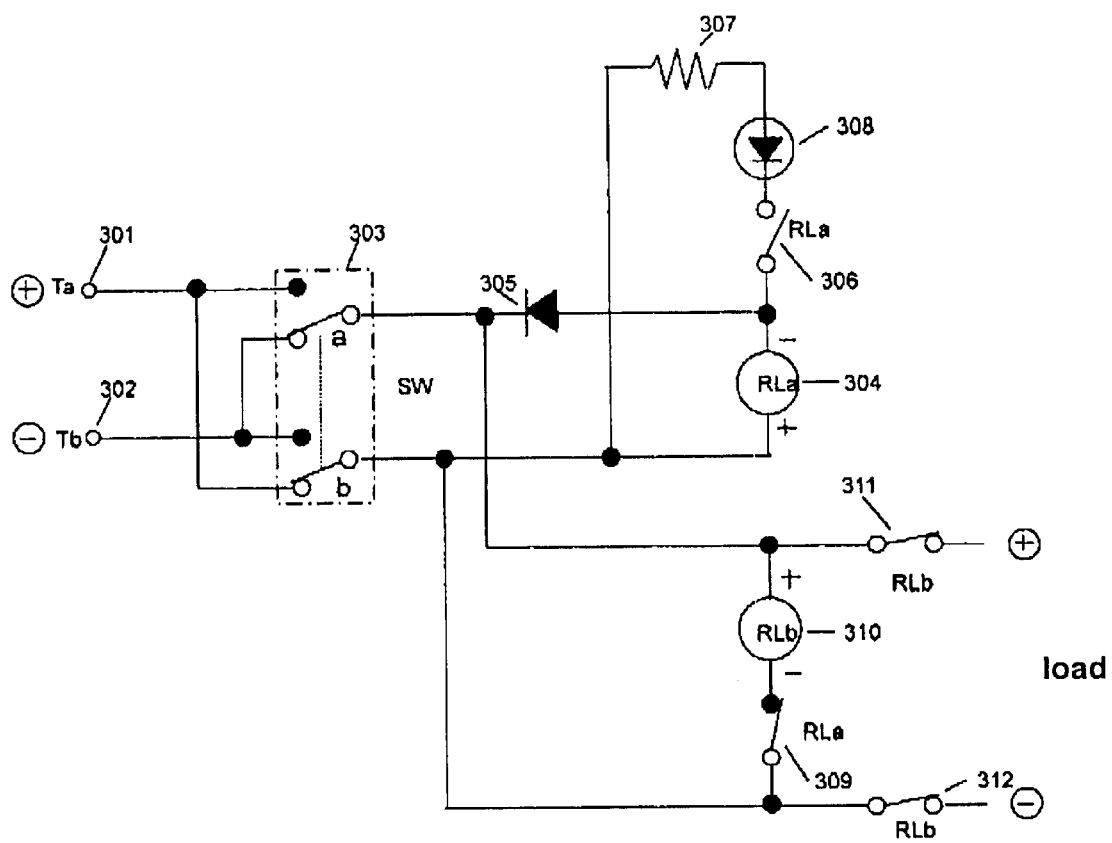
FIG. 3 is a circuit diagram of a power supply input section of a DC source drive type portable X-ray fluorescence analyzer of the present invention.

By switching the switch 203, it is possible to alternate a supply path of the DC power supply input to Ta 201 and Tb 202 to circuitry beyond the switch 203. FIG. 3 shows the state of the power supply input section circuitry when DC input polarity is switched by the switch for alternating the input power source supply path. At this time, since the contact point 306 of the relay a is opened, the LED 208 is not illuminated. Also, since another contact point 309 of relay a is closed, current flows in relay b310, and the contact points 311 and 312 of relay b are closed so that power of the correct polarity is supplied to the load.

Figure 4:
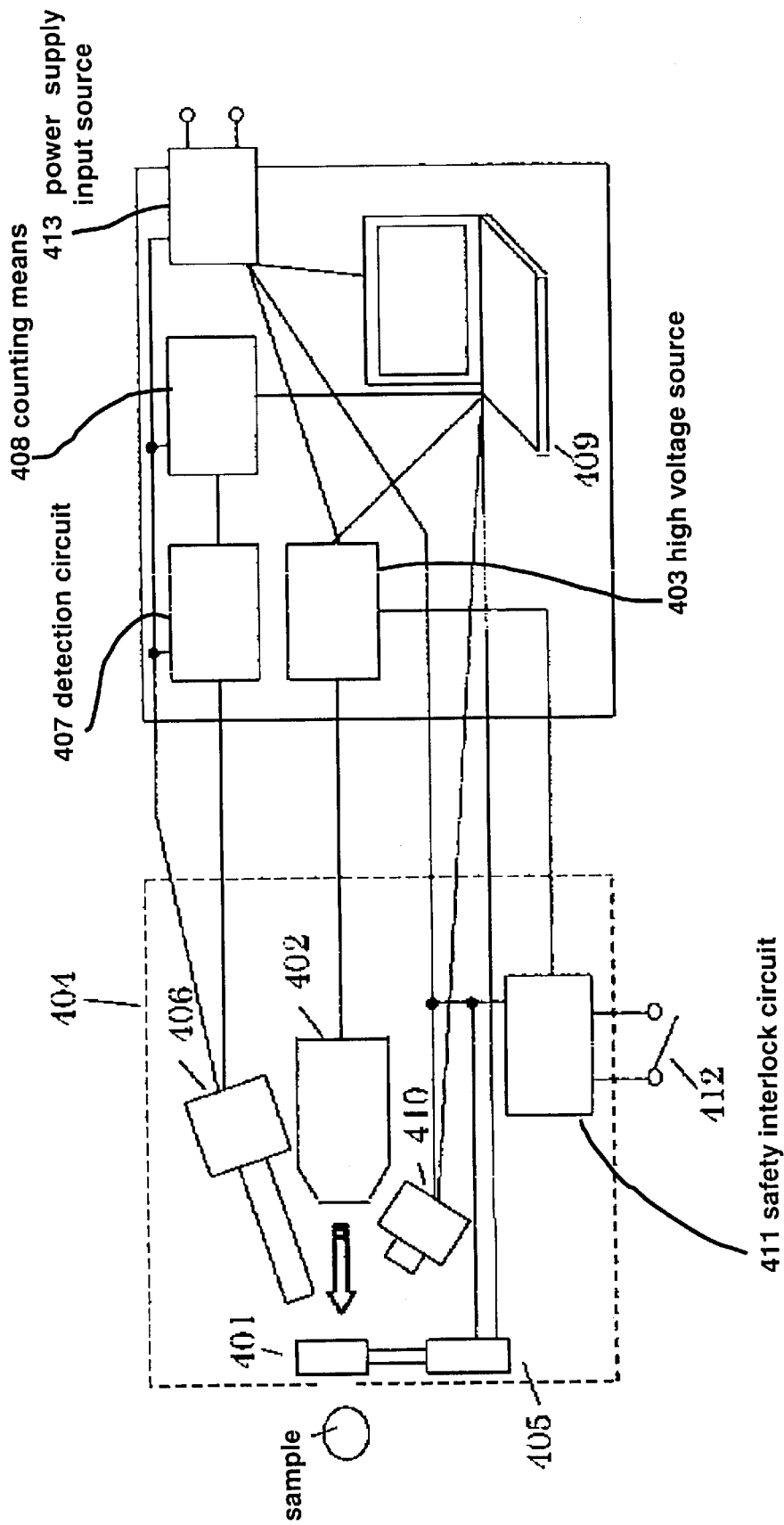
FIG. 4 is an overall schematic diagram of a DC source drive type portable X-ray fluorescence analyzer.

FIG. 4 shows an overall structure of a DC source drive type portable X-ray fluorescence analyzer. A shutter 401 in FIG. 4 is made of metal of a sufficient thickness to be able to completely shield against X-rays. An X-ray vessel 402 is realized as a small lightweight device by adopting an end window type small X-ray vessel. Luminous flux of X-ray fluorescence generated from the X-ray tube 402 that receives a high voltage supply from a high voltage source 403 passes through a roentgenization space provided in a measurement head housing 404 of the X-ray fluorescence analyzer, and is irradiated onto a sample to be measured, but while measurement is not in progress the X-rays are shielded by the shutter 401 and there is no leakage of X-rays to parts outside the measurement head. The shutter 401 is mechanically operated by an actuator 405 such as a solenoid. Luminous flux of secondary emissions of fluorescence X-rays from the sample to be measured by X-ray irradiation are taken in by an X-ray detector 406, converted to an electrical pulse signal and transmitted to a subsequent detection circuit 407. As the X-ray detector 406, it is possible to use a semiconductor detector of Si or Ge, a scintillation detector, or a proportional counter tube etc., depending on the purpose of measurement. In the detection circuit 407, an inputted electrical pulse signal is amplified so as to make it a level signal that is easy to process later. Appropriate waveform adjustment processing so as to ensure a required counting rate and obtain a favorable energy resolution is also performed at this time. The wave height of the electrical pulse after this processing has been performed is converted to a digital value by an A/D converter, and then passed to subsequent counting means 408. In the counting means 408, the number of electrical pulses inputted during the measurement period is counted for every peak-to-peak. Successively detected secondary X-ray fluorescence is then expressed as a spectrum, with the Y-axis representing the number of X-ray counts, i.e., energy.

Analysis such as movement instructions for the shutter 401, output condition settings to the high voltage source 403, and display of count results is implemented by a computer 409.

In order to irradiate primary X-rays on sections to be measured, it is necessary to accurately position the measurement head housing 404. An imaging device 410, such as a CCD camera, is provided on the measurement head housing 404 side, and by optically observing the sample to be measured, a positional relationship between the sample to be measured and the measurement head housing 404 can be simply ascertained, and accurate measuring position alignment becomes possible.

When detecting anomalies in mounting states of the portable X-ray fluorescence analyzer and operational anomalies of components relating to device safety, the output of the high voltage source 403 is controlled, and a safety interlock circuit 411 is provided in the ordinary portable X-ray fluorescence analyzer, with the intention of stopping generation of X-rays. The generation and stopping of X-rays is instructed using X-ray key switch 412, but with respect to stopping X-rays, operation of the safety interlock circuit 411 has priority.

The high voltage power supply 403, actuator 405, X-ray detector 406, detection circuit 407, counting means 408, computer 409, imaging device 410 and safety interlock circuit 411 of FIG. 4 operate by receiving power from the power supply input circuit 413 of this embodiment.

Figure 5:
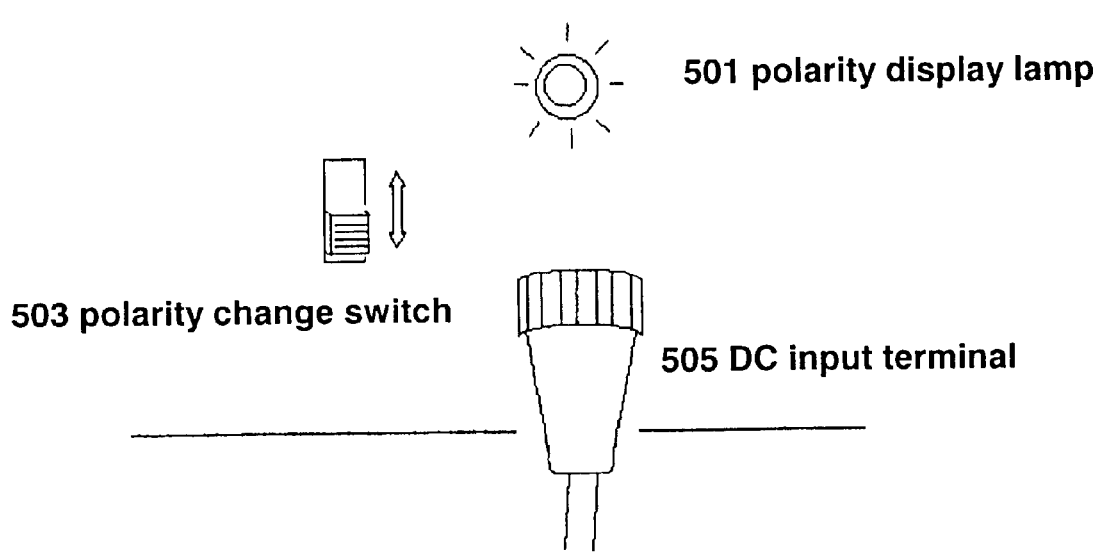
FIG. 5 shows an embodiment of polarity display means and switch means.

FIG. 5 shows an example where a polarity display lamp 501, being the polarity display means described above, and a polarity change switch 503, being the above described switch means 6, are arranged in a DC input terminal 505. This polarity display lamp 501 corresponds to the above described LED 208.

By thus being arranged on the side of the DC input terminal 505, it is made easy to recognize the polarity.

In a DC power supply driven portable X-ray fluorescence analyzer provided with a power supply input section, by having a polarity discrimination means for discriminating the polarity of a DC power supply input to the power supply input section, and polarity display means for displaying the polarity of the input DC power according to the output of the polarity discriminating means, it is made possible to immediately know the polarity of an input DC power source.

Also, by providing reverse connection protection means for preventing supply of input current to a load side when input indicating that the DC power supply has reverse polarity is detected from the polarity discrimination means, it is possible to prevent damage to the device.

Further, because of the switch means for switching a current path of input current and supplying a correct polarity power supply to a load when input indicating that the DC power supply has negative polarity is detected from the polarity discrimination means, it is possible to change over to a state in which the device can be used by a single switch operation.

Accordingly, the power supply input circuit of present invention makes it possible to provide a portable X-ray fluorescence analyzer that has a simple power supply operation and can be readily implemented.

What is claimed is:

1. A DC source drive type portable X-ray fluorescence analyzer having a load section including an X-ray source and an X-ray detector, a power supply input section for receiving a DC power supply input, and a power supply section for supplying power to the load section, the power supply input section comprising:

polarity discrimination means for discriminating a polarity of the DC power supply input to the power supply input section; and polarity display means for displaying the polarity of the input DC power supply according to an output from the polarity discrimination means.

2. The portable X-ray fluorescence analyzer of claim 1; further comprising reverse connection protection means for preventing the supply of current to the load section when the polarity discrimination means indicates that the DC power supply input has a negative polarity.

3. The portable X-ray fluorescence analyzer of claim 1; further comprising switch means for switching a current path from the DC power supply input to the load section, so as to reverse the polarity of the DC power supply input, and supplying the reversed polarity DC power supply to the load section when the polarity discrimination means indicates that the DC power supply input has a negative polarity.

4. A DC source drive type portable X-ray fluorescence analyzer provided with a power supply input section, comprising:

polarity discrimination means for discriminating a polarity of a DC power supply input to the power supply input section;

a polarity display lamp for displaying the polarity of the DC power supply input according to an output from the polarity discrimination means; and a polarity change switch for switching a current path from the DC power supply input to the load section, so as to reverse the polarity of the DC power supply input, and supplying the reversed polarity DC power supply to a load when the polarity discrimination means indicates that the DC power supply has a negative polarity.

5. The portable X-ray fluorescence analyzer of claim 1; wherein the polarity discrimination means comprises a relay and a diode connected in series between input terminals to which the DC power supply input is supplied, the diode being biased to allow current flow in only one direction.

6. The portable X-ray fluorescence analyzer of claim 5; wherein the one direction corresponds to a negative polarity of the DC power supply input.

7. The portable X-ray fluorescence analyzer of claim 5; wherein the polarity display means comprises a switch activated by the relay of the polarity discrimination means, and a light emitting device connected to the switch to become illuminated when a current flows through the relay.

8. The portable X-ray fluorescence analyzer of claim 1; further comprising a measurement head housing; an X-ray source provided in the measurement head housing for producing an X-ray beam to irradiate a sample located outside the measurement head housing through an opening therein; a shutter provided in the measurement head housing; an actuator for selectively activating the shutter to allow the X-ray beam to pass through the opening; an X-ray detector provided in the measurement head housing for detecting fluorescent X-rays from the sample; and a high voltage power source for supplying power to the X-ray source.

9. A portable X-ray analyzer driven by a DC input voltage, comprising: a measurement head housing; an X-ray source provided in the measurement head housing for producing an X-ray beam to irradiate a sample located outside the measurement head housing through an opening therein; a shutter provided in the measurement head housing; an actuator for selectively activating the shutter to allow the X-ray beam to pass through the opening; an X-ray detector provided in the measurement head housing for detecting fluorescent X-rays from the sample; a high voltage power source for supplying power to the X-ray source; and a power supply input section for receiving a DC input voltage and supplying DC voltage to respective components of the X-ray analyzer, the power supply input section comprising a polarity detecting circuit for detecting a polarity of the DC input voltage, a polarity display lamp for displaying the polarity of the DC input voltage according to an output of the polarity detecting circuit, and a polarity change switch for reversing the polarity of the DC input voltage when the polarity detecting circuit indicates that the DC input voltage has a negative polarity.

10. A portable X-ray analyzer according to claim 9; wherein the polarity detecting circuit comprises a relay and a diode connected in series between input terminals to which the DC input voltage is supplied, the diode being biased to allow current flow in only one direction.

11. A portable X-ray analyzer according to claim 10; wherein the one direction corresponds to a negative polarity of the DC power supply input.

* * * * *